May 9, 1972 L. RODHOUSE Plant Pat. 3,159
WALNUT TREE
Filed July 22, 1970
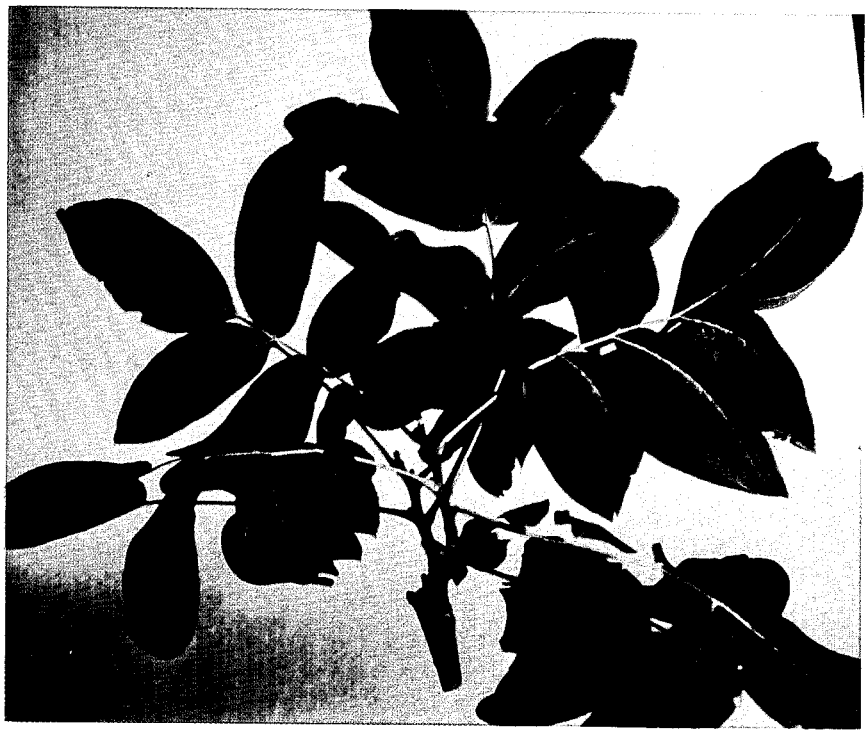
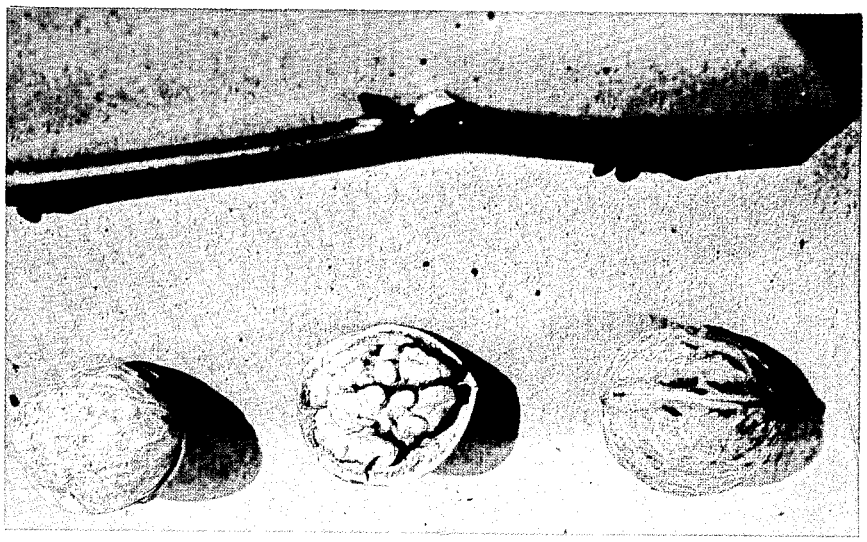
Inventor.
Louis Rodhouse
By: Robb & Robb
Attorneys.

United States Patent Office

Plant Pat. 3,159
Patented May 9, 1972

3,159

WALNUT TREE

Louis Rodhouse, Pleasant Hill, Ill., assignor to Stark Bros. Nurseries & Orchards Company, Louisiana, Mo.

Filed July 22, 1970, Ser. No. 57,375
Int. Cl. A01h *5/03*
U.S. Cl. Plt.—32 1 Claim

The present invention relates to a new and distinct variety of walnut tree which originated on my cultivated property located at Pleasant Hill, in Pike County, Ill., as a seedling which was derived from a nut of a Carpathian walnut variety of unknown parentage brought into the United States from Poland.

My attention was attracted and devoted to this particular seedling because although it most nearly resembles the walnut variety known as "Lake" (unpatented), it bore nuts more heavily but slightly smaller than the "Lake" variety, and otherwise was characterized by a unique combination of commercially valuable features which distinguish the new seedling from all other varieties of which I am aware, as evidenced by the following features which are outstanding therein:

(1) A heavy nut bearing habit and consistently good annual nut crops;
(2) Good hardiness to cold temperatures as low as −20° F. without injury;
(3) Excellent flavor qualities of the nuts, with no bitter taste;
(4) An attractive light color of the kernels which is retained during proper storage of the nuts;
(5) A self-fertile habit when grown in isolation from other walnut varieties.

Asexual reproduction of my new walnut variety by grafting, as performed by me in Pike County, Ill. and on my behalf in Pike County, Mo., shows that the foregoing characteristics and distinctions come true and are established and transmitted through succeeding propagations.

The accompanying drawing shows typical specimens of the wood, foliage and nuts of my new walnut variety, with a portion of the shell of one of the nut specimens removed to expose the kernel, as depicted in color as nearly true as it is reasonably possible to make the same in a color illustration of this character.

The following is a detailed description of my new variety, with color terminology in accordance with Ridgway's Color Standards and Nomenclature, as based on specimens grown and observed in Pike County, Ill.:

Parentage: A cultivated seedling of a Carpathian walnut variety of unknown parentage.

Propagation: Holds its distinguishing characteristics through succeeding propagations by grafting.

Dates of first and last pickings: October 1 and October 15, respectively.

Maturity season: First 2 weeks in October, in Pike County, Ill.

Tree: Large; medium vigorous; hardy (has withstood temperatures as low as −20° F. without apparent injury); very productive.

*Growth habit.*—Vigorous; heavy limbs.

*Wood.* — One-year wood — Color — Olive Brown, Plate XL, Color No. 17‴, tone M. Older wood—Color—Light Olive Gray, Plate LI, Color No. 23′, tone d.

*Foliage.*—Abundant; large; heavy.

*Buds.*—Short; rounded. Color—Olive Brown, Plate XL, Color No. 17‴, tone M, with heavy pubescence.

Nuts:

*Ripening.*—Even. Time of harvesting—First half of October.

*Quantity.*—Abundant.

*Maturity.*—Early.

*Tenacity.*—Free.

*Cluster.*—Not clustered; bears nuts singly.

*Size.*—Medium large. Length—1½ inches. Diameter—$1\frac{5}{16}$ x 1¼ inches.

*Weight.*—Average number of nuts to pound—about 35.

*Shape.*—Base—round. Point—blunt.

*Shell.*—Thin; cracks and releases easily. Color—Chamois, Plate XXX, Color No. 19″, tone b.

*Kernel.*—Flavor—good. Shape—round. Sutures—uneven. Color—Warm Buff, Plate XV, Color No. 17′, tone d.

I claim:

1. A new and distinct variety of walnut tree, substantially as herein shown and described, characterized particularly as to novelty by the unique combination of a heavy nut bearing habit and consistently good annual nut crops, good hardiness to cold temperatures as low as −20° F. without injury, excellent flavor qualities of the nuts, with no bitter taste, an attractive light color of the kernels which is retained during proper storage of the nuts, and a self-fertile habit when grown in isolation from other walnut varieties.

No references cited.

ROBERT BAGWILL, Primary Examiner